United States Patent
Yang

(10) Patent No.: US 10,682,413 B2
(45) Date of Patent: Jun. 16, 2020

(54) PHARMACEUTICAL FORMS OF DIAZABICYCLOOCTANE DERIVATIVES AND PROCESS FOR PRODUCING THE SAME

(71) Applicants: Fedora Pharmaceuticals Inc., Edmonton (CA); Meiji Seika Pharma Co., Ltd., Tokyo (JP)

(72) Inventor: Kewei Yang, Basel (CH)

(73) Assignees: FEDORA PHARMACEUTICALS INC., Edmonton, Alberta (CA); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 16/140,608

(22) Filed: Sep. 25, 2018

(65) Prior Publication Data

US 2019/0091336 A1 Mar. 28, 2019

Related U.S. Application Data

(60) Provisional application No. 62/563,819, filed on Sep. 27, 2017.

(51) Int. Cl.
| | |
|---|---|
| *A61K 47/26* | (2006.01) |
| *A61K 31/437* | (2006.01) |
| *A61K 31/439* | (2006.01) |
| *A61K 9/19* | (2006.01) |

(52) U.S. Cl.
CPC ............. *A61K 47/26* (2013.01); *A61K 9/19* (2013.01); *A61K 31/437* (2013.01); *A61K 31/439* (2013.01)

(58) Field of Classification Search
CPC .............................. A61K 47/26; A61K 31/437
USPC ............................................................ 514/300
See application file for complete search history.

(56) References Cited

U.S. PATENT DOCUMENTS

| | | | | |
|---|---|---|---|---|
| 8,796,257 B2 * | 8/2014 | Maiti | .......... | C07D 519/00 514/210.21 |
| 9,181,250 B2 * | 11/2015 | Abe | .......... | A61K 45/06 |
| 2015/0203503 A1 * | 7/2015 | Patil | .......... | A61K 31/439 514/2.4 |
| 2016/0272641 A1 | 9/2016 | Abe et al. | | |

FOREIGN PATENT DOCUMENTS

| | | |
|---|---|---|
| CN | 101264088 | 9/2008 |
| EP | 0 438 747 | 7/1991 |
| EP | 1 448 234 | 8/2004 |
| EP | 3 067 355 | 9/2016 |
| EP | 3 228 620 | 10/2017 |
| WO | 2015/046207 | 4/2015 |
| WO | 2015/053297 | 4/2015 |
| WO | 2015046207 | * 4/2015 |
| WO | 2015053297 | * 4/2015 |
| WO | 2016/088863 | 6/2016 |
| WO | 2016/116878 | 7/2016 |
| WO | 2016/120752 | 8/2016 |
| WO | 2016/151543 | 9/2016 |

OTHER PUBLICATIONS

Morinaka et al., Journal of Antimicrobial Chemotherapy (2015), 70(10), 2779-2786.*
International Search Report and Written Opinion, dated Jan. 30, 2019, of international application No. PCT/IB2018/001185.
International Search Report and Written Opinion, dated Dec. 19, 2018, of international application No. PCT/IB2018/001187.
International Search Report and Written Opinion, dated Dec. 20, 2018, of international application No. PCT/IB2018/001204.
Baheti A. et al. "Excipients used in lyophilization of small molecules", J. Excipients Food Chem. 1(1):41-54 (2010).
Brittain H.G. et al. "Methods for the Characterization of Polymorphs", pp. 235 and 237 of Polymorphism in Pharmaceutical Solids, published by M. Dekker, New York, NY USA (1999).
Caira M.R. et al. "Crystalline Polymorphism of Organic Compounds" Topics in Current Chemistry 198:163-208 (1998).
Einfalt T. et al. "Methods of amorphization and investigation of the amorphous state" Acta Pharma. 63:305-334 (2013).
Kumar D.R. et al. "Formulation and Evaluation of Lyophilized Antibacterial Agent", Int. J. PharmTech Res. 5(4):1581-1589 (2013).
Morinaka et al., "OP0595, a new diazabicyclooctane: mode of action as a serine beta-lactamase inhibitor, antibiotic and beta-lactam 'enhancer'", J. Antimicrob. Chemo. 70:2779-2786 (2015).

* cited by examiner

*Primary Examiner* — Niloofar Rahmani
(74) *Attorney, Agent, or Firm* — Wenderoth, Lind & Ponack, L.L.P.

(57) ABSTRACT

The present invention relates to a pharmaceutical composition and a lyophilisate of a diazabicyclooctane derivative represented by Compound I, a process for producing the same and methods for using the same.

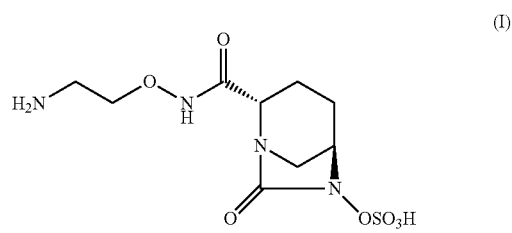

(I)

21 Claims, 2 Drawing Sheets

PHARMACEUTICAL FORMS OF DIAZABICYCLOOCTANE DERIVATIVES AND PROCESS FOR PRODUCING THE SAME

CROSS-REFERENCE TO RELATED APPLICATIONS

The present application claims the benefit of priority to U.S. Provisional Application No. 62/563,819 filed on Sep. 27, 2017, the entire contents of which is hereby incorporated by reference.

ACKNOWLEDGMENT OF GOVERNMENT SUPPORT

This invention was made with government support under Contract No. HHSO100201600038C awarded by the U.S. Department of Health and Human Services. The government has certain rights in the invention.

BACKGROUND

Penicillins and cephalosporins are β-lactam antibiotics that are widely and frequently used in the clinic. However, the acquisition of resistance to β-lactam antibiotics by various pathogens has had a damaging effect on maintaining the effective treatment of bacterial infections. The most significant known mechanism related to the acquisition of bacterial resistance is the production of class A, C, and D β-lactamases having a serine residue at the active center. These enzymes decompose the β-lactam antibiotic, resulting in the loss of the antimicrobial activities. Class A β-lactamases preferentially hydrolyze penicillins while class C β-lactamases have a substrate profile favoring cephalosporins.

Commercially available β-lactamase inhibitors, e.g., clavulanic acid, sulbactam, and tazobactam, are known and these inhibitors are effective mainly against class A β-lactamase producing bacteria, and used as a mixture with a penicillin antibiotic. However, 250 types or more of β-lactamases have been reported to date, including resistant bacteria which produce class A KPC-2 β-lactamase decomposing even carbapenem.

In recent years, infectious diseases caused by the above-mentioned resistant bacteria as pathogenic bacteria are found not only in severe infectious disease but also occasionally in community-acquired infectious disease. The currently available β-lactamase inhibitors are insufficient to inhibit the incessantly increasing β-lactamase and novel β-lactamase inhibitors that are required for the difficult treatment of bacterial infectious diseases caused by resistant bacteria. The development of antibacterial agents as well as β-lactamase inhibitors is in strong demand as the commercially available inhibitors become increasingly ineffective.

One of these antibacterial agents, (2S, 5R)—N-(2-aminoethoxy)-7-oxo-6-(sulfooxy)-1,6-diazabicyclo[3.2.1]octane-2-carboxamide, represented by Compound (I), is a "potent, broad-spectrum, non-β-lactam β-lactamase inhibitor" useful for antibiotic-resistant Gram-negative bacteria (Li, H.; Estabrook, M.; Jacoby, G. A.; Nichols, W. W.; Testa, R. T.; Bush, K. *Antimicrob Agents Chemother* 2015, 59, 1789-1793.) There are four crystalline forms of (2S, 5R)—N-(2-aminoethoxy)-7-oxo-6-(sulfooxy)-1,6-diazabicyclo[3.2.1]octane-2-carboxamide previously characterized and known in the art (see, e.g., International Publication no. WO 2015/053297).

While other crystalline forms have been previously characterized, large scale-up manufacturing processes which afford good reproducibility, high stability and high yield have not been achieved. When developing technologies for a commercial process, there are several factors and properties to consider when converting a small-scale lab process to a large manufacturing process suitable for clinical use.

A particular pharmaceutical composition may be preferable in certain circumstances in which certain aspects, such as ease of preparation, stability, etc., are deemed to be critical. In other situations, a different pharmaceutical composition may be preferred for greater solubility and/or superior pharmacokinetics.

SUMMARY

The present application relates to a pharmaceutical composition and a lyophilisate for intravenous infusion directed to a diazabicyclooctane derivative represented by (2S, 5R)—N-(2-aminoethoxy)-7-oxo-6-(sulfooxy)-1,6-diazabicyclo[3.2.1]octane-2-carboxamide, also referred to as "Compound (I)," and process for producing the same. Methods of treating bacterial infections by administering the pharmaceutical composition are also described:

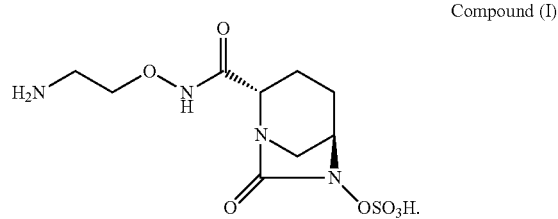

Compound (I)

In an aspect, the present application provides a pharmaceutical composition comprising a lyophilisate of a compound represented by Compound (I) and a bulking agent, wherein the ratio of Compound (I) and the bulking agent is between 0.1:1 to 10:1 (mg/mL). In an embodiment, the ratio of Compound (I) and the bulking agent is 5:1 (mg/mL). In an embodiment, the ratio of Compound (I) and the bulking agent is 3:1 (mg/mL). In an embodiment, the ratio of Compound (I) and the bulking agent is 2:1 (mg/mL). In an embodiment, the ratio of Compound (I) and the bulking agent is 1:1 (mg/mL).

In an embodiment, the pharmaceutical composition comprises a bulking agent wherein the bulking agent is a sugar. In an embodiment, the pharmaceutical composition comprises a bulking agent wherein the bulking agent is sucrose. In another embodiment, the pharmaceutical composition comprises a bulking agent wherein the bulking agent is trehalose dihydrate. In an embodiment, the pharmaceutical composition comprises a bulking agent wherein the bulking agent is mannitol. In an embodiment, the pharmaceutical composition comprises a lyophilisate that is an amorphous lyophilisate. In another embodiment, the pharmaceutical composition comprises a sterile solvent suitable to reconstitute the lyophilisate and suitable for parenteral administration.

In another aspect of the invention, the present application provides a process for preparing a pharmaceutical composition comprising a lyophilisate of Compound (I) and a bulking agent, wherein the ratio of Compound (I) and the bulking agent is between 0.1:1 to 10:1 (mg/mL), the process comprising lyophilizing an aqueous solution of Compound (I) in the presence of a bulking agent wherein the step of lyophilizing comprises (a) freezing the solution; (b) drying the frozen solution to form a product by decreasing the vacuum pressure and increasing the temperature of the frozen solution; and then, a second drying of the product by increasing the temperature of the product.

In an embodiment, the ratio of Compound (I) and the bulking agent is 5:1 (mg/mL). In an embodiment, the ratio of Compound (I) and the bulking agent is 3:1 (mg/mL). In an embodiment, the ratio of Compound (I) and the bulking agent is 2:1 (mg/mL). In an embodiment, the ratio of Compound (I) and the bulking agent is 1:1 (mg/mL).

In an embodiment of the process for preparing the pharmaceutical composition, the freezing step is at a temperature of at least −30° C.±5° C. or colder. In another embodiment, the freezing step is at a temperature of −40° C.±5° C. In another embodiment of the process for preparing the pharmaceutical composition, the freezing step is maintained at a temperature of at least −30° C.±5° C. for at least 3 hours. In an embodiment of the process for preparing the pharmaceutical composition, the pressure is reduced to 30 mTorr after the freezing step. In an embodiment of the process for preparing the pharmaceutical composition, the first drying step is increased to a temperature of at least −25° C.±5° C. or warmer. In another embodiment of the process for preparing the pharmaceutical composition, the second drying step is increased to a temperature of at least 10° C.±5° C. or warmer. In an embodiment, the temperature of the second drying step is maintained for least 8 hours at 30 mTorr.

In an embodiment, the process comprises a lyophilisate of Compound (I) and a bulking agent wherein the bulking agent is sucrose. In an embodiment, the process comprises a lyophilisate of Compound (I) and a bulking agent wherein the bulking agent is trehalose dihydrate. In an embodiment, the process comprises a lyophilisate of Compound (I) and a bulking agent wherein the bulking agent is mannitol.

In an aspect of the invention, the present application provides a method treating a bacterial infection in a subject in need thereof comprising administering to the subject a therapeutically effective amount of a pharmaceutical composition of Compound (I) according to the pharmaceutical composition comprising a lyophilisate of Compound (I) and a bulking agent, wherein the ratio of Compound (I) and the bulking agent is between 0.1:1 to 10:1 (mg/mL). In an embodiment, the ratio of Compound (I) and the bulking agent is between 1:1 and 5:1 (mg/mL). In an embodiment, the ratio of Compound (I) and the bulking agent is 2:1 (mg/mL).

In an embodiment, the method of treating a bacterial infection comprising administering to the subject the pharmaceutical composition in an amount sufficient to inhibit a bacterial β-lactamase. In another embodiment, the method of treating a bacterial infection wherein the β-lactam antibiotic comprises a penicillin, a cephalosporin, or a monobactam. In an embodiment, the method of treating a bacterial infection wherein the subject is human.

In an embodiment, the β-lactam antibiotic is a penicillin. In another embodiment, the β-lactam antibiotic is a cephalosporin. In an embodiment, the β-lactam antibiotic is a monobactam. In an embodiment, the subject in need thereof is a human.

In another embodiment the β-lactam is a β-lactam antibiotic and comprises a core selected from penam, carbapenam, oxapenam, penem, carbapenem, monobactam, cephem, carbacephem and oxacephem.

In another embodiment the β-lactam antibiotic is selected from ampicillin, amoxicillin, azidocillin, azlocillin, aztreonam, biapenem, carbeniccilin, carfecillin, carindacillin, carumonam, cefepime, cefotaxim, cefsumide, ceftaroline, ceftolozane ceftriaxone, ceftazidime, cephem, doripenem, ertapenem, flomoxef, meropenem, piperacillin, tazobactam, ticarcillin, and tigermonam, or pharmaceutically acceptable salts or esters thereof.

In yet another embodiment the β-lactam antibiotic is meropenem, or a pharmaceutically acceptable salt or ester thereof.

The compounds are useful in the treatment of bacterial infections in humans or animals either alone or in combination with β-lactam antibiotics and/or with other non β-lactam antibiotics.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION

Figure 1:
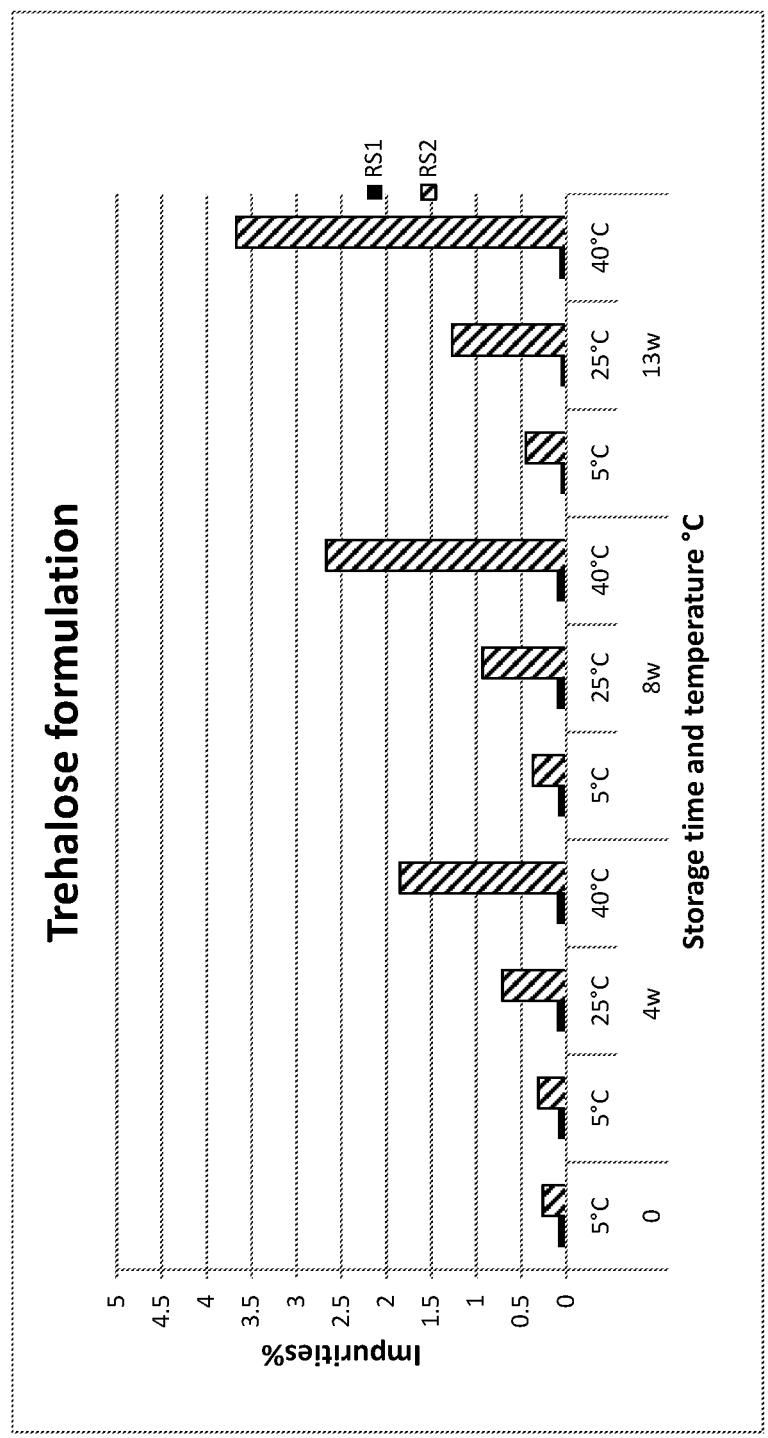
FIG. 1 illustrates the results of a stability study over a period of 13 weeks at various temperatures for a trehalose dihydrate formulation.

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

DEFINITIONS

As used herein, and unless noted to the contrary, the following terms and phrases have the meaning noted below.

The lyophilisate of Compound (I) can exist in various isomeric forms, as well as in one or more tautomeric forms, including both single tautomers and mixtures of tautomers. The term "isomer" is intended to encompass all isomeric forms of a compound of this invention, including tautomeric forms of the compound. The term "tautomer" refers to a proton shift from one atom of a molecule to another atom of the same molecule.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The present invention contemplates various stereoisomers and mixtures thereof and includes "enantiomers", which refers to two stereoisomers whose molecules are nonsuperimposeable mirror images of one another.

If there is a discrepancy between a depicted structure and a name given to that structure, then the depicted structure controls. Throughout the present application, Compound (I) is used interchangeably with (2S, 5R)—N-(2-aminoethoxy)-7-oxo-6-(sulfooxy)-1,6-diazabicyclo[3.2.1]octane-2-carboxamide. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat," "treating" and "treatment" refer to the amelioration or eradication of a disease or symptoms associated with an infectious disease. In certain embodiments, such terms refer to minimizing the spread or worsening of the infectious disease resulting from the administration of one or more prophylactic or therapeutic agents to a patient with such an infectious disease.

The term "effective amount" refers to an amount of a compound of the invention or other active ingredient sufficient to provide a therapeutic or prophylactic benefit in the treatment or prevention of an infectious disease or to delay or minimize symptoms associated with an infectious disease. Further, a therapeutically effective amount with respect to a compound of the invention means that amount of therapeutic agent alone, or in combination with other therapies, that provides a therapeutic benefit in the treatment or prevention of an infectious disease. Used in connection with a compound of the invention, the term can encompass an amount that improves overall therapy, reduces or avoids symptoms or causes of disease, or enhances the therapeutic efficacy or synergies with another therapeutic agent. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient must undergo chemical conversion by metabolic processes before becoming an active pharmacological agent. Exemplary prodrugs of compounds in accordance with Compound (I), are esters, acetamides, and amides.

The lyophilisate of Compound (I) may be isotopically-labelled by having one or more atoms replaced by an atom having a different atomic mass or mass number. Examples of isotopes that can be incorporated into Compound (I) include isotopes of hydrogen, carbon, nitrogen, oxygen, phosphorous, fluorine, chlorine, or iodine. Illustrative of such isotopes are $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled lyophilisates Compound (I), therefore, are useful in drug and/or tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}C$, $^{18}F$, $^{15}O$ and $^{13}N$ provides labeled analogs of the inventive compounds that are useful in Positron Emission Tomography (PET) studies, e.g., for examining substrate receptor occupancy. Isotopically-labeled compounds can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of Compound (I). Such products may result from, for example, the oxidation, reduction, hydrolysis, amidation, esterification, dimerization and like processes primarily due to enzymatic activity upon administration of the composition. Accordingly, the invention includes compounds that are produced as by-products of enzymatic or non-enzymatic activity on a composition of Compound (I) following the administration of such a composition to a mammal for a period of time sufficient to yield a metabolic product. Metabolic products, particularly pharmaceutically active metabolites are typically identified by administering a radiolabelled compound of the composition in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of a pharmaceutical composition of a lyophilisate of Compound (I). Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-amino salicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the composition. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the composition may be true solvates, while in other cases, the compound of the composition may merely retain adventitious water or be a mixture of water plus some adventitious solvent.

According to the series of production processes of the present invention, pharmaceutical compositions of a compound represented by the aforementioned Compound (I), particularly the lyophilisate, can be produced with good reproducibility and high yield.

In one aspect, substantially pure polymorph forms of the present invention are provided. For example, the present invention includes an amorphous form as described in this application that is about ≥95% pure. For example, the forms may be about ≥95%, ≥96%, ≥97%, ≥98% or ≥99% pure.

In some embodiments, the lyophilisate of Compound (I) is isolated in a substantially pure form. The API described herein may have purity of more than about 90%, about 91%, about 92%, about 93%, about 94%, about 95%, about 96%, about 97%, about 98%, or about 99% by weight. In a further embodiment, the API may have a purity of more than about 95% by weight. For example, the API may be ≥95%, ≥96%, ≥97%, ≥98% or ≥99% pure.

Pharmaceutical Formulations

In one embodiment, lyophilized Compound (I) is formulated as pharmaceutically acceptable compositions that contain the amorphous form in an amount effective to treat a particular disease or condition of interest upon administration of the pharmaceutical composition to a mammal. Pharmaceutical compositions in accordance with the present invention can comprise lyophilized Compound (I), in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a liquid. The carrier(s) may be liquid, with the compositions being, for example, an injectable liquid or an aerosol, which is useful in, for example, inhalatory administration.

In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for delivery by injection. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for parenteral administration should contain an amount of a compound of the invention such that a suitable dosage will be obtained.

As discussed above, parenteral formulations include Compound (I) and excipients. Optionally, at least two excipients (e.g., two, three, or more excipients) are included in the pharmaceutical composition. Excipients for use in the pharmaceutical composition include, but are not limited to, sugars, salts, amino acids, divalent cations, and surfactants. These excipients can contribute to the stability of the formulation. In some examples, the use of these excipients in the pharmaceutical composition and thus in the parenteral formulations allows for the long-term storage of the pharmaceutical composition (e.g., storage for twelve months or greater) without loss of Compound (I) activity.

Suitable sugars for use in the pharmaceutical compositions described herein include, for example, monosaccharides and disaccharides. In some examples, the pharmaceutical composition include mannitol, sorbitol, sucrose, trehalose dihydrate or combinations of these. Further examples of suitable sugars include lactose, dextrose, fructose, glucose, and maltose.

The sugars for use in the pharmaceutical composition and/or lyophilized formulations can include one sugar or a combination of two or more sugars. For example, the pharmaceutical composition can include sucrose as the sugar present in the formulation or can include a combination of mannitol and sorbitol as the sugars present in the formulation. The concentration of excipients, including sugars, present in the lyophilized formulations can be expressed herein as the weight percent based on the weight of the liquid pharmaceutical composition (i.e., the pharmaceutical composition, prior to lyophilization, including a liquid carrier). The total concentration of sugar(s) present in the pharmaceutical composition can be 10% by weight or less based on the weight of the pharmaceutical composition. For example, the total concentration of sugars can be less than 7.5% by weight based on the weight of the liquid pharmaceutical composition (e.g., less than 7.4% by weight, less than 7.3% by weight, less than 7.2% by weight, less than 7.1% by weight, less than 7% by weight, less than 6% by weight, less than 5% by weight, less than 4% by weight, less than 3% by weight, less than 2% by weight, or less than 1% by weight based on the weight of the liquid pharmaceutical composition). For example, sucrose can be present in the pharmaceutical composition in a concentration ranging from 0.1% to 5%, from 1% to 4.5%, or from 2% to 4% (e.g., 3%) by weight based on the weight of the liquid pharmaceutical composition.

Lyophilization can be performed using techniques and equipment as known in the art. The lyophilization process can be performed, for example, using a lyophilizer. Lyophilizing can involve freezing and subsequently drying the liquid pharmaceutical formulation. Optionally the lyophilization involves a product loading stage, freezing stage and primary drying and secondary drying stage. The product is loaded into the lyophilizer and the shelves are set to a target temperature set-point for a pre-determined duration. The freezing stage involved the shelves being chilled to a target set point at a controlled rate (° C./hr). The product is maintained at the freezing stage for a pre-determined amount of time. In the freezing step, the liquid pharmaceutical formulation can be cooled, for an appropriate period of time, to a temperature lower than 0° C. to form a frozen product. Optionally, the liquid pharmaceutical formulation can be cooled to a temperature of −50° C. or lower.

In some examples, the liquid pharmaceutical formulation can be cooled for 10 hours or less. For example, the pharmaceutical formulation can be cooled for 9 hours or less, 8 hours or less, 7 hours or less, 6 hours or less, 5 hours or less, 4 hours or less, 3 hours or less, 2 hours or less, 1 hour or less, or 30 minutes or less.

Optionally, the lyophilization process can include an annealing step wherein the frozen pharmaceutical formulation is warmed to a temperature at or below ambient temperature, and then cooled again to form a frozen product. In some examples, the annealing step is not performed.

The frozen product can then be dried under reduced pressure (e.g., by applying a vacuum) to form the lyophilized pharmaceutical formulation. Optionally, a vacuum pressure ranging from 30 to 80 μm Hg (e.g., 50 μm Hg) can be applied to the frozen pharmaceutical formulation.

The drying step can be performed at a temperature at, below, or above ambient temperature. For example, the drying step can be performed at a temperature of 40° C. or less, 30° C. or less, 20° C. or less, 10° C. or less, or 0° C. or less. Optionally, the lyophilized pharmaceutical formulation can be further dried in one or more additional drying steps at a temperature at, below, or above ambient temperature to remove residual water. For example, the additional drying steps can be performed at a temperature ranging from −10° C. to 50° C. (e.g., from 0° C. to 40° C., from 10° C. to 30° C., or from 20° C. to 25° C.). Furthermore, the lyophilized pharmaceutical formulation can be dried in the presence of an inert gas (e.g., nitrogen) or a combination of inert gasses. For example, the lyophilization vessel and/or the pharmaceutical storage container can be purged with an inert gas and capped to avoid exposure of the pharmaceutical formulation to the air. The lyophilized pharmaceutical formulation, after one or more drying steps, can have a moisture content of, for example, less than 20%. In some examples, the moisture content of the lyophilized pharmaceutical formulation is less than 15%, less than 10%, less than 5%, less than 4%, less than 3%, less than 2%, less than 1%, less than 0.5%, or less than 0.1%.

The lyophilized pharmaceutical formulations are stable, for example, at a temperature at about ambient temperature for a period of time (e.g., at least one day). In some examples, the pharmaceutical formulations are stable at a temperature of about 4° C. or lower for at least three months (e.g., at least four months, at least five months, at least six months, at least seven months, at least eight months, at least nine months, at least ten months, at least eleven months, at least twelve months, at least thirteen months, at least fourteen months, at least fifteen months, at least sixteen months, at least seventeen months, at least eighteen months, or any amount of time greater than three months). Additionally described herein are methods of preparing the pharmaceutical formulation as described herein and then lyophilizing the formulation to prepare a lyophilized pharmaceutical formulation. The pharmaceutical formulations prepared according to these methods include low levels of particulates and are thus suitable for administration by parenteral infusion or injection. In some examples, the levels of particulates in the methods are determined using the light obscuration particle count test and/or the microscopic particle count test according to USP <788>, which is incorporated herein in its entirety.

The pharmaceutical composition of the invention may include various materials, which modify the physical form of a solid or liquid dosage unit.

The pharmaceutical composition of the invention in liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

Therapeutic Use

The compounds of the composition, or their pharmaceutically acceptable salts or esters, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the composition, or pharmaceutically acceptable salts or esters thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. Where separate dosage formulations are used, the compounds of the composition and one or more additional active agents can be administered at essentially the same time, i.e., concurrently, or at separately staggered times, i.e., sequentially; combination therapy is understood to include all these regimens.

Therapeutically effective dosages of lyophilized Compound (I), or a pharmaceutical composition of lyophilized Compound (I), will generally range from about 1 to 2500 mg/day, from about 10 to about 1500 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined and is within the skills and judgment of the ordinary clinician or physician. In any case the compound or composition will be administered at dosages and in a manner which allows a therapeutically effective amount to be delivered based upon patient's unique condition.

The term "β-lactam antibiotic" refers to a compound with antibiotic property that contains a β-lactam functionality. Examples of β-lactam antibiotics which can be used in combination with the compounds of the present invention represented by Compound (I), are commonly marketed penicillins, cephalosporins, penems, carbapenems and monobactams.

Examples of β-lactam antibiotics which can be used in combination with the compounds of the present invention represented by Compound (I), are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine, latamoxef (moxalactam), and CXA-101. From the carbapenem class of β-lactam antibiotics such as imipenem, meropenem, panipenem, biapenem, doripenem, ertapenem and the like could be used. From monobactam class of β-lactam antibiotics such as aztreonam, carumonam, tigemonam, and the like could be used as the combination partner of antibiotic.

EXAMPLES

The present application is directed to a pharmaceutical composition of Compound (I) suitable for parenteral administration. The title compound, Compound (I), undergoes decomposition and dimerization in aqueous solutions, thus a lyophilisate formulation was developed. Applicant discovered a lyophilisate formulation comprising a sugar and Compound (I) to afford an amorphous lyophilisate suitable for intravenous administration.

In an aspect, the present application provides an amorphous lyophilisate formulation comprising Compound (I) and a sugar, such as trehalose dihydrate, sucrose and mannitol and methods for making the same. Several bulking agents were tested as excipients for amorphous lyophilisate products. In the present application, sucrose, trehalose dihydrate and mannitol were tested at a concentration of 50 mg/mL, while the concentration of the API was fixed at 100 mg/mL (see Table 1). The lyophilisate formulations were developed to provide a glass transition temperature (Tg') relatively higher than −30° C., excellent batch homogeneity and good stability. The $T_g'$ of these three formulations was analyzed using differential scanning calorimetry (DSC) and the collapse temperature ($T_{collapse}$) was analyzed using Freeze-drying Microscope. All three formulations have $T_g'$ above −30° C. (see Table 2). Additionally, all batches were found to be homogeneous with respect to lyophilisate cake appearance.

TABLE 1

Example lyophilization process for a trehalose-containing formulation

| Step | Shelf temperature (° C.) | Ramp Duration (° C./min) | Hold Time (h) | Pressure (mTorr) |
|---|---|---|---|---|
| Pre-Cooling | 5 | | 1 | ambient |
| Freezing | −40 | 0.3 | 3 | ambient |
| vacuum | −40 | | 0.5 | 30 |
| Primary Drying | −25 | 0.2 | 70 h | 30 |
| Secondary Drying | +25 | 0.2 | 8 h | 30 |

TABLE 2

Tg' and Tcollapse of sugar-containing formulations.

| No. | API concentration | Bulking agent | Tg' ° C. | Tcollapse (full) ° C. |
|---|---|---|---|---|
| 1 | 100 mg/mL | Sucrose 50 mg/mL | −27.7 | −21.0 |
| 2 | 100 mg/mL | trehalose dihydrate 50 mg/mL | −26.2 | −21.5 |
| 3 | 100 mg/mL | mannitol 50 mg/mL | −19.9 | −15.8 |

Potential organic impurities in Compound (I) are generally related to the manufacture and may be starting materials, precursors, intermediates, degradation products of the parent compound, or by-products of reagents. During the course of the development of the API, stability studies showed the presence of three main impurities characterized and referred to as "RS1" which represents a degradation product, {[(6-[(2-aminoethoxy)carbamoyl]piperdin-3-yl)amino]oxy}sulfonic acid; "RS2" which represents an adduct of Compound (I), ((1-(6-((2-aminoethoxy)carbamoyl)piperidin-3-yl)-3-(2-((7-oxo-6-(sulfooxy)-1,6-diazabicyclo[3.2.1]octane-2-carboxamido)oxy)ethyl)ureido)oxy)sulfonic acid; and "RS3" which represents another by-product, 2-((2-(tert-butylamino)ethoxy)carbamoyl)-7-oxo-1,6-diazabicyclo[3.2.1]octan-6-yl hydrogen sulfate. The present formulation was developed in order to increase the stability of the aqueous solution and thus minimize the presence of the impurities. Applicant discovered that the molar ratio of API to sugar had an impact on the $T_{collapse}$ and $T_g'$ to afford a formulation with excellent stability. Higher $T_g'$ and $T_{collapse}$ enables a higher freezing temperature during manufacturing, reduces lyophilization cake collapse risk, ensures batch homogeneity and provides ease of manufacture.

Figure 2:
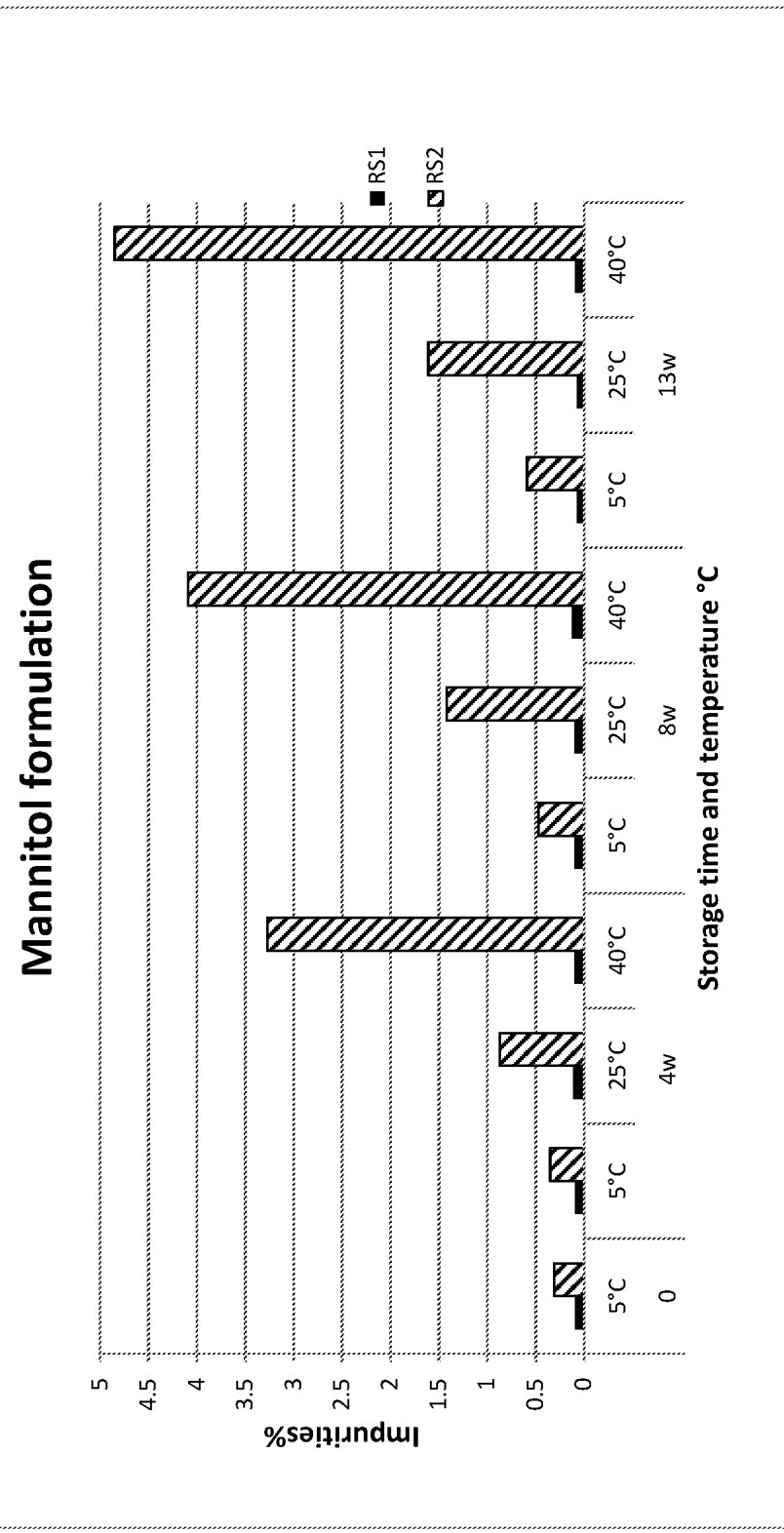
FIG. 2 illustrates the results of a stability study over a period of 13 weeks at various temperatures for a mannitol formulation.

The lyophilisate formulations were subjected to stability studies, the results of which are illustrated in Table 3, Table 4, FIG. 1 and FIG. 2. Table 3 illustrates data over a period of 1 month. Table 4 illustrates data for another technical batch over a period of 1 year whereas FIG. 1 and FIG. 2 illustrate studies which were conducted over a period of 13 weeks at various temperatures for a trehalose dihydrate formulation and mannitol formulation, respectively.

TABLE 3

Data for Drug Product Stability Technical Batches after 1 month

| | | | Degradation products in area % | | | | |
|---|---|---|---|---|---|---|---|
| | Content per vial by HPLC | | RS1 | RS2 | Impurity 3 | Total | Total of All |
| Acceptance Criterion | 90.0%-110.0% of label claim | 450.0-550.0 mg | ≤1.70% | ≤1.85% | ≤0.10% | ≤0.50% | ≤4.10% |
| Initial Analysis | 100.4% | 502.2 | ≤0.05% | 0.22% | ≤0.05% | ≤0.05% | 0.22% |
| | | 1 Months | | | | | |
| −20° C. | 98.5% | 492.3 | ≤0.05% | 0.26% | ≤0.05% | ≤0.05% | 0.26% |
| 2-8° C. | 98.5% | 492.4 | ≤0.05% | 0.37% | ≤0.05% | ≤0.05% | 0.37% |
| 25° C./60% Relative humidity | 97.6% | 487.8 | ≤0.05% | 1.05% | ≤0.05% | ≤0.05% | 1.05% |

TABLE 4

Data for Drug Product Stability Technical Batches over a period of 1 year

| | Time | | | | | | | | |
|---|---|---|---|---|---|---|---|---|---|
| | T0 | 4 w | | 10 w | | | 26 w | | 52 w |
| | | | | Storage Temperature | | | | | |
| | initial | −20° C. | 2-8° C. | −20° C. | 2-8° C. | 25° C. | −20° C. | 2-8° C. | −20° C. | 2-8° C. |
| Main peak | 99.7 | 99.8 | 99.7 | 99.8 | 99.5 | 98.2 | 99.7 | 99.3 | 99.7 | 99.1 |
| RS1 | ≤0.05 | ≤0.05 | ≤0.05 | ≤0.05 | 0.07 | 0.08 | 0.06 | 0.06 | 0.06 | ≤0.05 |
| RS2 | 0.19 | 0.18 | 0.28 | 0.21 | 0.40 | 1.30 | 0.24 | 0.61 | 0.25 | 0.79 |
| RS3 | ≤0.05 | nd | Nd | ≤0.05 | ≤0.05 | ≤0.05 | ≤0.05 | ≤0.05 | ≤0.05 | ≤0.05 |
| Total of all degr. Products | 0.19 | 0.18 | 0.28 | 0.21 | 0.47 | 1.38 | 0.30 | 0.67 | 0.30 | 0.79 |

The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A pharmaceutical composition comprising a lyophilisate of a compound represented by Compound (I):

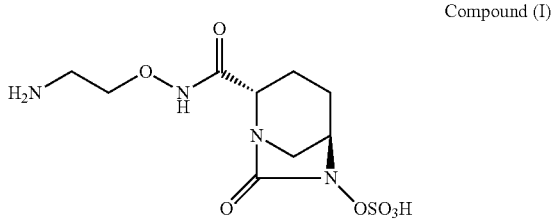

Compound (I)

and a bulking agent, wherein the ratio of Compound (I) and the bulking agent is between 0.1:1 to 10:1 (mg/mL).

2. The pharmaceutical composition of claim 1, wherein the ratio of Compound (I) and the bulking agent is 3:1 (mg/mL).

3. The pharmaceutical composition of claim 1, wherein the ratio of Compound (I) and the bulking agent is 2:1 (mg/mL).

4. The pharmaceutical composition of claim 1, wherein the ratio of Compound (I) and the bulking agent is 1:1 (mg/mL).

5. The pharmaceutical composition of claim 1, wherein the bulking agent is sucrose, trehalose, dehydrate or mannitol.

6. A process for preparing a pharmaceutical composition comprising a lyophilisate of a compound represented by Compound (I):

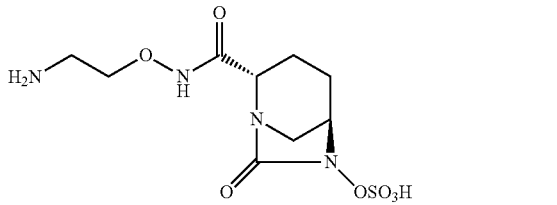

Compound (I)

and a bulking agent, wherein the ratio of Compound (I) and the bulking agent is between 0.1:1 to 10:1 (mg/mL), the process comprising lyophilizing an aqueous solution of Compound (I) in the presence of a bulking agent wherein the step of lyophilizing comprises:

(a) freezing the solution;
(b) drying the frozen solution to form a product by lowering the vacuum pressure and increasing the temperature of the frozen solution; and, then
(c) a second drying of the product by increasing the temperature of the product.

7. The process according to claim 6, wherein the ratio of Compound (I) and the bulking agent is 3:1 (mg/mL).

8. The process according to claim 6, wherein the ratio of Compound (I) and the bulking agent is 2:1 (mg/mL).

9. The process according to claim 6, wherein the ratio of Compound (I) and the bulking agent is 1:1 (mg/mL).

10. The process according to claim 6, wherein the freezing step is at a temperature of at least $-30°$ C.$\pm 5°$ C. or colder.

11. The process according to claim 6, wherein the freezing step is at a temperature of $-40°$ C.$\pm 5°$ C.

12. The process according to claim 6, wherein the pressure is reduced to 30 mTorr after the freezing step.

13. The process according to claim 6, wherein the temperature of the drying step of (b) is increased to at least $-25°$ C.$\pm 5°$ C. or warmer.

14. The process according to claim 6, wherein the temperature of the second drying step of (c) is increased to at least $10°$ C.$\pm 5°$ C. or warmer.

15. The process according to claim 6, wherein the bulking agent is sucrose, trehalose dehydrate or mannitol.

16. A method for treating a bacterial infection in a subject in need thereof comprising administering to the subject a therapeutically effective amount of a pharmaceutical composition comprising a lyophilisate of a compound represented by Compound (I):

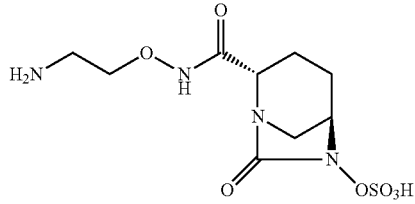

Compound (I)

and a bulking agent, wherein the ratio of Compound (I) and the bulking agent is between 0.1:1 to 10:1 (mg/mL).

17. The method according to claim 16, wherein the ratio of Compound (I) and the bulking agent is between 1:1 to 3:1 (mg/mL).

18. The method according to claim 16, wherein the ratio of Compound (I) and the bulking agent is 2:1 (mg/mL).

19. The method according to claim 16 for treating a bacterial infection in a subject in need thereof comprising administering to the subject the pharmaceutical composition in amount sufficient to inhibit a bacterial β-lactamase.

20. The method according to claim 16, further comprising administering to the subject a therapeutically-effective amount of a β-lactam antibiotic.

21. The method according to claim 20, wherein the β-lactam antibiotic comprises a penicillin, a cephalosporin, or a monobactam.

* * * * *